United States Patent [19]

Zotti et al.

[11] 4,288,554

[45] Sep. 8, 1981

[54] PROCESS FOR THE CULTIVATION OF YEAST CELLS

[75] Inventors: Aldo Zotti; Giuliano Cardini, both of Milan, Italy

[73] Assignee: Euteco Impianti S.p.A., Milan, Italy

[21] Appl. No.: 105,486

[22] Filed: Dec. 20, 1979

[51] Int. Cl.³ .............................................. C12N 1/32
[52] U.S. Cl. ................................... 435/247; 435/255; 435/813; 435/921
[58] Field of Search .................... 426/69, 60; 435/247, 435/813, 255, 921

[56] References Cited

U.S. PATENT DOCUMENTS

| | | | |
|---|---|---|---|
| 3,901,762 | 8/1975 | Yoshikawa et al. | 435/247 X |
| 3,934,039 | 1/1976 | Cardini et al. | 426/60 X |
| 4,003,790 | 1/1977 | Barnes et al. | 435/247 X |
| 4,021,304 | 5/1977 | Shimamatsu et al. | 435/247 X |
| 4,168,201 | 9/1979 | Wegner | 435/247 X |

*Primary Examiner*—R. B. Penland
*Attorney, Agent, or Firm*—Sughrue, Mion, Zinn, Macpeak and Seas

[57] ABSTRACT

Continuous process for the cultivation of yeast cells under aerobic conditions in an aqueous growth medium, to which an aqueous nutrient medium comprising a source of assimilable nitrogen and methanol of a source of assimilable carbon is continuously added. The yeast belongs to the species *Candida boidinii* and the nutrient medium comprises a primary source of assimilable nitrogen consisting of urea and a secondary source of assimilable nitrogen chosen from ammonia, ammonium hydroxide and ammonium salts, the ratio between nitrogen in the primary source and that in the secondary source being from 2:1 to 1:20.

11 Claims, No Drawings

PROCESS FOR THE CULTIVATION OF YEAST CELLS

The present invention relates to a process for the cultivation of yeasts in a nutrient medium containing methanol, particularly of yeasts suitable for foods both for man and for animals.

The production on an industrial scale of yeasts suitable for human and animal consumption, by means of their cultivation in nutrient media containing organic materials has been known for long. The industrial processes most known are based on a rapid multiplication of the yeast cells which increase, in aerobic conditions, at the expense of nutrient media containing, as well as mineral salts, particularly of phosphorus, also a source of assimilable carbon and a source of assimilable nitrogen.

These processes comprise essentially no inoculation stage of the nutrient medium with the micro-organism (yeast), a growth stage of the micro-organism and finally a stage for separation of the micro-organism from the growth medium.

In industrial practice the cultivation of the yeasts is generally carried out continuously, by delivering continuously an aqueous nutrient medium to the fermentation medium, previously inoculated, and discharging continuously a flow of fermented broth with a suitable concentration of cells.

The cells are then separated from the broth by usual techniques, such as flocculation, decanting, filtration and centrifuging, and then purified.

Traditionally, the materials usable as assimilable carbon sources for the production of yeasts are mainly chosen from molasses, sulphite lye, wood hydrolysates and vegetable refuse. These materials are not available in large quantities. Moreover, their supply is difficult and non-constant, in that it is often linked to harvests and to the course of the weather.

In order to overcome these disadvantages more recently there have been proposed new, alternative sources of carbon, such as the paraffins, particularly the fraction having on an average from 10 to 30 atoms of carbon per molecule, and methanol.

Recently, various causes have increase the interest toward methanol as a carbon source for the cultivation of yeasts. As is known, methanol is a compound obtainable economically in any degree of purity from a mixture of hydrogen and carbon monoxide, the so called synthesis gas, prepared from the most varied carbonaceous compounds and from steam.

When nutrient media containing methanol as the source of assimilable carbon are used, in order to have a sufficiently high growth rate of the micro-organism it is necessary that the concentration of the methanol in the fermenting apparatus be maintained at high levels. However, it has been ascertained that beyond relatively modest methanol concentrations, the conversion into useful products is gradually reduced as the methanol concentration is increased.

The exact explanation of this phenomenon is not known. It seems, however, that with the increase in the methanol concentration a metabolism of the microorganism prevails which, rather than using the methanol for the production of new yeast cells, transforms non-negligible quantities of methanol into products not useful for the production of yeast.

Of these products, formaldehyde and formic acid are particularly harmful. When present at high concentrations both in the broth and within the cells, they have a toxic action on the micro-organism which adds to that of the methanol, producing a lowering of the yield. Therefore, it is difficult to achieve both a high velocity of transformation of the methanol and a high yield of useful fermentation products when using nutrient media containing methanol.

The usual sources of nitrogen in the nutrient media are ammonia and urea. The use of ammonia is desirable in that it is economic; however, ammonia does not favour the achievement of high yields of useful product, particularly when methanol is present in high concentration; these drawbacks occur to a lesser extent with urea; however the cost of urea renders its use disadvantageous.

The present invention is essentially based on the discovery that the joint use of ammonia, $NH_4OH$ or ammonium salts, and urea in well defined ratios, in the cultivation of yeast in a nutrient medium containing methanol allows the achievement of high yields together with high values of the rate of growth.

Under these conditions the phenomena observed above are eliminated or at least reduced. It is surprising that the joint use of ammonia and urea according to the process of the present invention allows yields greater than those which are obtained with only ammonia, and even greater than those which are obtained with only urea, with a satisfactory rate of transformation.

Thus, the invention provides a continuous process for the cultivation of yeast cells in an aqueous growth medium and under aerobic conditions, in which an aqueous nutrient medium comprising a source of assimilable nitrogen and methanol as a source of assimilable carbon is continuously delivered to a fermenting vessel containing the growth medium, and in which a stream of growth medium is continuously discharged from said vessel with recovery of the yeast cells present therein, characterized by using a yeast of the species *Candida boidinii* and using a nutrient medium comprising a primary source of assimilable nitrogen consisting of urea, and a secondary source of assimilable nitrogen consisting of one or more compounds chosen from the group consisting of ammonia, ammonium hydroxide and ammonium salts, the ratio between nitrogen in the primary source and that in the secondary source being from 2:1 to 1:20.

The maintenance in the feed of nutrient medium of a ratio of from 2:1 to 1:20, and preferably from 1:1 to 1:10, between nitrogen in the primary source and nitrogen in the secondary source is an essential characteristic of the process of the invention. Generally, best results are obtained by maintaining this ratio at a value of from 1:1 to 1:2, values of about 1:1.5 being preferred.

Advantageously the secondary source of assimilable nitrogen consists of ammonium salts, and preferably ammonium sulphate. It is also possible to use ammonia as a secondary source of assimilable nitrogen, or to use a mixture of ammonium salt with ammonia, the latter being introduced into the growth medium in amounts such as to kept the pH value within the desired range.

Generally, the growth medium is maintained at a temperature of from 26° to 33° C., the residence time in the fermenting vessel is maintained at a value of from 6 to 10 hours and the pH is maintained at a value of from 3 to 6, and preferably from 3 to 5, values of the order of 5 being generally preferred. The pH is preferably maintained at a constant value within the range shown. The control of the pH value may be carried out by means of the immission into the growth medium of potassium or sodium hydroxide. As indicated above, ammonia may also be used with advantage for the purpose, in the gaseous form or in solution.

In order to obtain satisfactory values of the growth rate it is still necessary to maintain the methanol content of the growth medium at values of at least 10 ppm, and preferably of the order of 50 ppm.

In addition nutritive salts, mainly or potassium, phosphorus, sulphur and magnesium, as well as micro-elements such as calcium, iron, manganese, zinc, molybdenum, sodium, copper, boron, rhodium and cobalt are introduced into the growth medium. Thus the potassium may be fed in as potassium chloride, phosphate, citrate, sulphate, acetate or nitrate, and the magnesium as the sulphate or chloride. The phosphorus and the sulphur may be fed in either as phosphoric acid or alkali metal or ammonium phosphates, and as alkali metal and alkaline earth metal sulphates, respectively.

Finally, small amounts of growth activators, such as yeast extracts, vitamins, molasses and the like, may be added to the growth medium.

A further characteristic of the process of the present invention consists of the use of a yeast of the species *Candida Boidinii*, a species already classified as non-pathogenic. In practice the methanol, together with the mineral salts and the nitrogen sources, is dissolved in an aqueous solution, generally with a concentration of from 3 to 10% by weight. The solution, to which may be added, as growth agents, small quantities of yeast extract and vitamins, is fed continuously to the fermenting vessel, previously sterilised at about 120° C. and subsequently cooled.

The urea may be sterilised together with the salts or preferably alone by means of heating, or, still more preferably alone by means of filtration with a sterilising membrane. The ammonium salts are preferably sterilised together with the nutrient salts.

The fermentation is started with the loading of a yeast culture (micro-organism), prepared under sterile conditions. The oxygen necessary for the growth is provided by means of the blowing in of sterile air.

The fermentation is carried out continuously in a strongly aerated aqueous medium, and under agitation, for example in a reactor with an agitator with blades or of the "air-lift" type, under aseptic conditions and with or without over-pressure.

The operating conditions for the fermenting apparatus are rigorously controlled. The temperature is maintained at the values indicated by removing the heat developed in the growth of the microorganism by means of an exchanger. For this purpose the exchanger may be arranged inside the fermenting apparatus or the culture broth may be recirculated continuously through an external exchanger.

From the fermenting vessel there is discharged continuously the culture broth which is separated from the suspended yeast which is then washed and dried.

In the preferred embodiment an initial separation of the liquid is carried out, for example by centrifuging, the liquid being recirculated, so as to obtain a more concentrated suspension of the yeast, of the order of 10-15% by weight, referred to the dry matter.

The suspension obtained is then washed with water, either de-mineralised or even simply drinking water, reconcentrated by centrifuging up to a concentration of the order of 15-20% by weight and then subjected to a de-vitalising treatment.

This de-vitalising treatment may be carried out by heating the aqueous suspension of the cells, in a suitable reactor or directly in line, to a temperature of from 60° to 80° C., these conditions being maintained for 5-20 minutes and the temperature then being brought back to ambient.

According to another, non-preferred embodiment, the suspension is sent directly for drying, without prior cooling. Without wishing to be bound to any theory, it seems that during the de-vitalising treatment several chemical modifications occur in the cells which lead in practice to improved nutritional properties of the finished product.

The suspension, after the de-vitalising treatment, is sent for drying. This latter may advantageously be carried out in a spray-dryer fed with hot air, for example as illustrated in U.S. Pat. No. 3,934,039.

By operating under these conditions, yields of between 0.40 and 0.42 Kg of dry yeast per Kg of methanol are generally obtained. Moreover, the greater part of the culture broth separated may be recycled.

The yeast cell content of the growth medium is generally from 0.5 to 5 wt.%. In practice, under preferred conditions of operation with cell concentrations in the growth medium of 1 to 3%, up to 90% of the broth may be recycled without reducing the growth of the yeasts, or having undesirable variations in the yields from the process, or in the chemical composition of the final product. The high proportion of the liquid recycled, and hence recovered, is reflected in the saving in the consumption of water and in the treatment of the liquid effluents.

The yeast obtained after drying is a very pure product without traces of residual methanol, which typically is in the form of a flowing, straw-coloured powder with a smell of yeast, free from extraneous odours and tastes; it may be agglomerated into granules of various sizes.

The content of raw protein is typically of the order of 60-65%, greater than that of soya flour which is about 44%. Moreover this protein has a high content of those amino-acids, called essential amino-acids, which animal organisms are not able to synthesis and which must therefore be provided in the diet. This leads to a high nutritive power, greater than that of the more common protein flours.

The yeast moreover contains fatty acids consisting for more than 95% of molecules with even numbers of carbon atoms and is therefore very similar, in this aspect, to fish and soya flours.

A further qualitative aspect relates to the high presence in the yeast of unsaturated fatty acids which are much more easily digestible and hence assimilable than saturated acids. A great part of the unsaturated acids are moreover essential acids, such as linoleic acid, which represents about ⅓ of the total of the fatty acids.

The unsaturated fatty acids, which all have even numbers of carbon atoms, are defined as essential acids, like certain amino-acids, in that the animal organism is not able to synthesis these and must receive these with the diet, have high biological activity and influence important vital processes.

As well as the components of the protein and lipid fractions, formed from carbon, hydrogen, nitrogen, oxygen, sulphur and phosphorus, there are present in the yeast, mineral salts resulting from the nutritive solution, which contribute to various extents in determining the biological value of the product.

The content of mineral salts is influenced, within certain limits, by the distribution of the mineral salts in the nutritive solution and may be subject to possible adjustments by operating on the nutritive solution itself.

At times it is necessary to add to the yeast methionine or calcium, this latter in amounts depending on its use and particularly on its ratio with phosphorus.

As is known, methionine is a very important amino-acid, a dearth of which is common to all yeasts and also to proteins of vegetable origin, such as soya flour, this reducing their biological value. Similarly, the inequalities of the calcium/phosphorus ratios in favour of phosphorus may cause disadvantages in the feed which are not negligible.

In such cases, according to one embodiment of the process of the present invention, methionine in the form of synthetic DL-methionine and/or calcium in the form of salts or of the hydrated oxide is added in the necessary quantities to the de-vitalised cell suspension, before this latter is subjected to the drying, conveniently in a spray-dryer.

In this manner, as well as restoring the equilibrium described above, one also obtains perfect homogenisation of the additives with the yeast, which is difficult to achieve otherwise.

The invention will now be illustrated by the following non-limitative examples. Examples 1 and 2 are given as a control, to illustrate the results achieved with ammonia alone and with urea alone, respectively.

The yeast used in the examples was the *Candida boidinii* strain described in Antoine van Leeuwenhoek—*Journal of Microbiology and Serology* Volume 42 (1976) N.4 pages 533–540 by R. Craveri et al and identified by the initials LI-70.

EXAMPLE 1 (Comparative)

Fermenting apparatus of 200 liter capacity, previously sterilized, was loaded with 100 liters of a sterile, aqueous nutrient growth medium containing per liter of demineralised water:

| | | |
|---|---|---|
| $(NH_4)_2SO_4$ | 5 | g/l |
| $KH_2PO_4$ | 2 | g/l |
| $MgSO_4 . 7H_2O$ | 0.5 | g/l |
| NaCl | 0.1 | g/l |
| $CuSO_4 . 5H_2O$ | 100 | γ/l |
| $ZnSO_4 . 7H_2O$ | 1000 | γ/l |
| $MnSO_4 . 5H_2O$ | 1000 | γ/l |
| $FeSO_4 . 7H_2O$ | 5 | mg/l |
| $CaCl_2 . 2H_2O$ | 100 | mg/l |
| $Na_2MoO_4 . 2H_2O$ | 100 | mg/l |
| Biotin | 5 | γ/l |
| Vit. B1 | 100 | γ/l |
| Methanol | 5 | g/l |

The fermenting apparatus was thermostatically controlled to 30° C.; after having started a blade agitator, sterile air was introduced in an amount of 0.5 volume/volume/minute and the automatic control for the pH, fixed at the value of 5.0, was connected.

The reaction was then started by the introduction into the fermenting apparatus of five liters of a culture of the strain LI-70 cited above, belonging to the species *Candida boidinii*, cultivated on a growth medium similar to that described for the fermenting apparatus.

As the yeasts were multiplying at the expense of the methanol, the pH of the medium tended to become more acid. The pH was maintained constant by means of the automatic addition of an aqueous ammoniacal solution, which as well as regulating the pH, also acted as additional source of nitrogen for the culture.

When the methanol concentration in the culture broth fell below 500 ppm, steps were taken to bring this back to the initial value of 5000 ppm by the addition of new methanol previously sterilized by filtration with a sterilizing membrane. The methanol concentration was determined by means of gas-chromatographic analysis of the culture broth. Successive additions of methanol were then carried out until the fermentation medium reached a cell content of about 10 g/l.

At this point the continuous process was started by delivering to the fermenting apparatus an aqueous nutrient medium at increasing rates, until steady conditions were reached. Under steady conditions, the fermenting apparatus was fed with 14 Kg/h of aqueous nutrient medium containing, for each liter of water:

| | | |
|---|---|---|
| nutrient nitrogen | 1 | g/l |
| $KH_2PO_4$ | 2 | g/l |
| $H_3PO_4$ (85%) | 0.9 | g/l |
| $MgSO_4 . 7H_2O$ | 1 | g/l |
| NaCl | 0.1 | g/l |
| $CuSO_4 . 5H_2O$ | 500 | γ/l |
| $ZnSO_4 . 7H_2O$ | 15 | mg/l |
| $MnSO_4 . 5H_2O$ | 15 | mg/l |
| $FeSO_4 . 7H_2O$ | 15 | mg/l |
| $CaCl_2 . 2H_2O$ | 100 | mg/l |
| $Na_2MoO_4 . 2H_2O$ | 500 | γ/l |
| Biotin | 5 | γ/l |
| Vit. B1 | 100 | γ/l |
| Methanol | 30 | g/l |

$(NH_4)_2SO_4$ was used as the source of nutrient nitrogen. Before entering the fermentation apparatus the nutrient medium was sterilized by means of heating in line at 130° C. for five minutes and subsequently cooled to ambient temperature. The vitamins were sterilized separately at 100° C. for fifteen minutes and added to the main feed after cooling.

All the lines were in every case previously sterilized by steam at a pressure of 2 Kg for 20 minutes. To maintain the pH at the prefixed value of 5.0, sterilized aqueous KOH was added in an automatic discontinuous manner.

The feed of air to the fermenting apparatus was then brought from values of 0.5 volumes/volume/minute to that of 1 volume/volume/minute.

By means of automatic apparatus based on a weight cell, there was discharged continuously from the fermenting apparatus reacted culture broth in quantities such as to maintain in the fermenting apparatus a constant quantity of culture medium equal to about 100 Kg.

The reacted broth discharged was centrifuged so as to obtain a concentrated suspension containing about 10% by weight of cells; this suspension was then washed with water and the again centrifuged until a milk containing about 20 wt.% of dry matter was obtained.

The water separated was recycled to the sterilization stage. The yeast milk was then de-vitalised by heating at a temperature of 70° C. for 10 minutes and then passed into a spray-dryer, using air with an inlet temperature of 250° C. and an outlet temperature of 100° C.

By operating in this manner there was obtained 0.37 Kg of yeast in powder form for each kg of methanol fed in.

EXAMPLE 2 (comparative)

The test described in Example 1 was repeated using the same amount of nutrient nitrogen, with the difference that the source of nutrient nitrogen was urea. The latter was sterilized separately by means of filtration through a sterilizing membrane and added to the cooled nutrient medium.

By operating under these conditions there were obtained 0.40 Kg of yeast in powder form for each Kg of methanol fed in.

EXAMPLE 3

The test described in Example 1 was repeated by using a small overall supply of nutrient nitrogen and two sources of nutrient nitrogen, the first source consisting of urea and the second of ammonium sulphate. The urea was sterilized as in Example 2. The ratio between nitrogen in the first source and nitrogen in the second source was about 1:10. There were thus obtained 0.40 Kg of yeast in powder form for each Kg of methanol fed in.

The product obtained after drying was in the form of a flowing, straw-coloured powder, free from taste, but with an odour of yeast, without traces of extraneous odours or tastes and with a water content of 5% by weight. The chemical composition of the yeast, expressed in weight percentage with respect to the dry matter content, was as follows:

TABLE 1

| | |
|---|---|
| Raw Protein | 62% |
| Raw Lipids | 5% |
| Fibre | 1% |
| Ashes | 7.5% |
| Non-nitrogeneous products | 24.5% |

The percentage of raw protein was expressed in the usual manner by multiplying the total percentage of nitrogen, measured according to the KJELDAHL method, by 6.25.

The raw lipids were determined on the ether extract of the yeast hydrolysed in an acid medium, the ashes as the residue after incineration of the product at 550° C., the fibre by the method of the Agronomical Station of WEENDE, the non-nitrogeneous products being the balance to 100%.

The amino acid distribution of the yeast expressed as number of grams for 16 grams of nitrogen, was as follows:

TABLE 2

| | |
|---|---|
| Cystine | 2.1 |
| Isoleucine | 4.8 |
| Leucine | 6.8 |
| Lysine | 7.2 |
| Methionine | 1.5 |
| Phenylalanine | 4.3 |
| Threonine | 4.8 |
| Tryptophan | 1.8 |
| Valine | 4.9 |
| Alanine | 5.3 |
| Arginine | 5.3 |
| Aspartic acid | 11.3 |
| Glutamic acid | 13.2 |
| Glycine | 4.1 |
| Histidine | 2.2 |
| Proline | 3.5 |
| Serine | 4.6 |
| Tyrosine | 4.1 |

The amino acids were determined by the methodology of SPACKMANN, STEIN and MORE (Anal. Chem. 30, 1190, 1958).

For the acid hydrolysis of the yeast the procedure of MOORE and STEIN (Methods in Enzymology 6, 819, 1963) was followed.

The cystine and the cysteine were determined as the cysteic acid according to the procedure proposed by MOORE (J. Biol. Chem. 238 235 (1963)).

The tryptophan was determined after alkaline hydrolysis of the yeast with barium hydroxide according to the NOTMANN method (J. Biol. Chem. 237, 1146, 1962).

The yeast contains fatty acids, about 95% of which consist of molecules with even numbers of carbon atoms and is therefore extremely similar, in this aspect, to fish and soya flours. Also unsaturated acids are present in high concentrations, similar to those normally encountered in soya flour.

The distribution of the fatty acids was as follows (in weight percent):

TABLE 3

| | |
|---|---|
| Capric acid ($C_{10}$) | 0.13 |
| Lauric acid ($C_{12}$) | 0.20 |
| Tridecanoic acid ($C_{13}$) | 0.34 |
| Myristic acid ($C_{14}$) | 0.28 |
| Pentadecanoic acid ($C_{15}$) | 0.39 |
| Palmitic acid ($C_{16}$) | 21.88 |
| Palmitoleic acid ($C_{16:1}$) | 18.72 |
| Heptadecanoic acid ($C_{17}$) | 1.70 |
| Heptadecenoic acid ($C_{17:1}$) | 2.03 |
| Stearic acid ($C_{18}$) | 1.38 |
| Oleic acid ($C_{18:1}$) | 23.06 |
| Linoleic acid ($C_{18:2}$) | 29.89 |
| Even acids | 95.54 |
| Uneven acids | 4.46 |
| Unsaturated acids | 73.70 |
| Saturated acids | 26.30 |

The analysis of the fatty acids was carried out by gas-chromatography and by mass spectrometry, using the ether extract, after acid hydrolysis and subsequent methylation. The qualitative determination and the attribution of the positions of unsaturation were effected by mass spectroscopy while the quantitative determination was made by gas-chromatographic measurement.

Analysis of the yeast was carried out to ascertain the possible presence of residues of methanol. The analyses carried out did not reveal the presence of methanol in amounts greater than the limits of sensitivity of the analytical method used (5 ppm). The determination of the methanol content was carried out by means of gas-chromatography of an aqueous extract obtained by treating the yeast with cold water (yeast/water ratio of about 1:5) for two hours under agitation and by filtering.

The search for methanol was even extended to possible methyl compounds such as esters of the fatty acids, by using the gas-chromatographic technique at high sensitivity: the results were negative.

EXAMPLE 4

The test described in Example 3 was repeated, with the only difference that the ratio between nitrogen in the first source and nitrogen in the second source was about 1:1.4.

There were thus obtained 0.42 Kg of yeast in powder form for each Kg of methanol fed in.

The product had substantially the same properties as in Example 3.

EXAMPLE 5

The test described in Example 3 was repeated, with the sole difference that the ratio between nitrogen in the first source and nitrogen in the second source was about 1:1.

There were thus obtained 0.40 Kg of yeast in powder form of each Kg of methanol fed in.

The product has substantially the same properties as in Example 3.

We claim:

1. In a continuous process for the cultivation of yeast cells in an aqueous growth medium and under aerobic conditions, in which an aqueous nutrient medium comprising a source of assimilable nitrogen and methanol as a source of assimilable carbon is continuously delivered to a fermenting vessel containing the growth medium, and in which a stream of growth medium is continuously discharged from said vessel with recovery of the yeast cells present therein, the improvement which comprises using a yeast of the species *Candida boidinii* and using a nutrient medium comprising a primary source of assimilable nitrogen consisting of urea and a secondary source of assimilable nitrogen consisting of one or more compounds chosen from the group consisting of ammonia, ammonium hydroxide and ammonium salts, the ratio between nitrogen in the primary source and that in the secondary source being from 2:1 to 1:20.

2. The process of claim 1, wherein said ratio between nitrogen in the primary source and nitrogen in the secondary source is from 1:1 to 1:10.

3. The process of claim 1, wherein said ratio between nitrogen in the primary source and nitrogen in the secondary source is from 1:1 to 1:2.

4. The process of claim 1, wherein the cultivation is carried out by maintaining the growth medium at a temperature of from 26° to 33° C., controlling the pH of the growth medium to a value of from 3 to 6, maintaining the methanol content of the growth medium at a value of at least 10 ppm and using a residence time in the fermenting vessel of from 6 to 10 hours.

5. The process of claim 4, wherein said methanol content is about 50 ppm.

6. The process of claim 4, wherein the pH value of the growth medium is about 5.

7. The process of claim 1, wherein the growth medium contains from 0.5 to 5 wt.% of yeast cells.

8. The process of claim 1, wherein ammonium sulphate is used as the secondary source of assimilable nitrogen.

9. The process of claim 1, wherein ammonia is used as the secondary source of assimilable nitrogen.

10. The process of claim 4, wherein the secondary source of assimilable nitrogen consists mainly of ammonium sulphate together with a minor amount of ammonia fed into the growth medium to control the pH value within the range of 3 to 6.

11. The process of claim 1, wherein the nutrient medium contains nutrient elements chosen from the groups consisting of potassium, phosphorus, sulphur, magnesium, calcium, iron, manganese, zinc, molybdenum, sodium, copper, boron, iodine and cobalt.

* * * * *